United States Patent
Wang

(10) Patent No.: US 10,073,092 B2
(45) Date of Patent: Sep. 11, 2018

(54) APPARATUS FOR ASSAY STRIP(S) WITH SPECIMEN LOADING TO MULTIPLE ZONES AND RELATED METHODS

(71) Applicant: Andrew Wang, San Diego, CA (US)

(72) Inventor: Andrew Wang, San Diego, CA (US)

( * ) Notice: Subject to any disclaimer, the term of this patent is extended or adjusted under 35 U.S.C. 154(b) by 97 days.

(21) Appl. No.: 15/047,974

(22) Filed: Feb. 19, 2016

(65) Prior Publication Data
US 2017/0242003 A1     Aug. 24, 2017

(51) Int. Cl.
| | | |
|---|---|---|
| *G01N 33/558* | (2006.01) | |
| *G01N 33/543* | (2006.01) | |
| *G01N 21/78* | (2006.01) | |
| *G01N 21/84* | (2006.01) | |
| *G01N 21/77* | (2006.01) | |

(52) U.S. Cl.
CPC .......... *G01N 33/558* (2013.01); *G01N 21/78* (2013.01); *G01N 21/8483* (2013.01); *G01N 33/54366* (2013.01); *G01N 2021/7759* (2013.01)

(58) Field of Classification Search
CPC ............. G01N 33/558; G01N 21/8483; G01N 33/54366; G01N 21/78
See application file for complete search history.

(56) References Cited

U.S. PATENT DOCUMENTS

| | | |
|---|---|---|
| 4,746,631 A | 5/1988 | Clagett |
| 4,981,786 A | 1/1991 | Dafforn et al. |
| 5,223,220 A | 6/1993 | Fan et al. |
| 6,156,271 A | 12/2000 | May |
| 6,248,598 B1 | 6/2001 | Bogema |
| 6,375,896 B1 | 4/2002 | Wuske et al. |
| 6,528,323 B1 | 3/2003 | Thayer et al. |
| 6,534,324 B1 | 3/2003 | Zin |
| 65,928,015 | 6/2003 | Zimmer |
| 7,090,803 B1 | 9/2006 | Gould et al. |
| 7,175,992 B2 | 2/2007 | Fong |
| 8,252,248 B2 | 9/2012 | Kramer |
| 8,361,808 B2 | 1/2013 | Wang |
| 8,507,260 B2 | 9/2013 | Alajem et al. |
| 8,709,792 B2 | 4/2014 | Saul et al. |
| 2007/0020768 A1* | 1/2007 | Rundstrom .......... G01N 33/543 436/514 |
| 2007/0092401 A1* | 4/2007 | Liao .................. A61B 10/0038 422/400 |
| 2015/0064800 A1* | 3/2015 | Chance .............. G01N 33/6863 436/501 |
| 2015/0198592 A1 | 7/2015 | Wang |

* cited by examiner

*Primary Examiner* — Melanie Yu Brown
(74) *Attorney, Agent, or Firm* — Buche & Associates, P.C.; John K. Buche; Bryce A. Johnson

(57) ABSTRACT

A lateral flow assay device that is defined by multiple loading zones, wherein a sample pad is located before and upstream from a conjugate pad and another sample pad is located after and downstream from the conjugate pad. This configuration allows for increased sensitivity for detecting an analyte in a specimen. The device may employ multiple collection pads or a single collection pad and the collection pads may be engaged with the sample pads in several manners, including but not limited to, pressing down on a cassette with collection pads onto a cassette with the test strips, or by sliding the collection pads along the cassette with the test strips and sample pads.

4 Claims, 3 Drawing Sheets

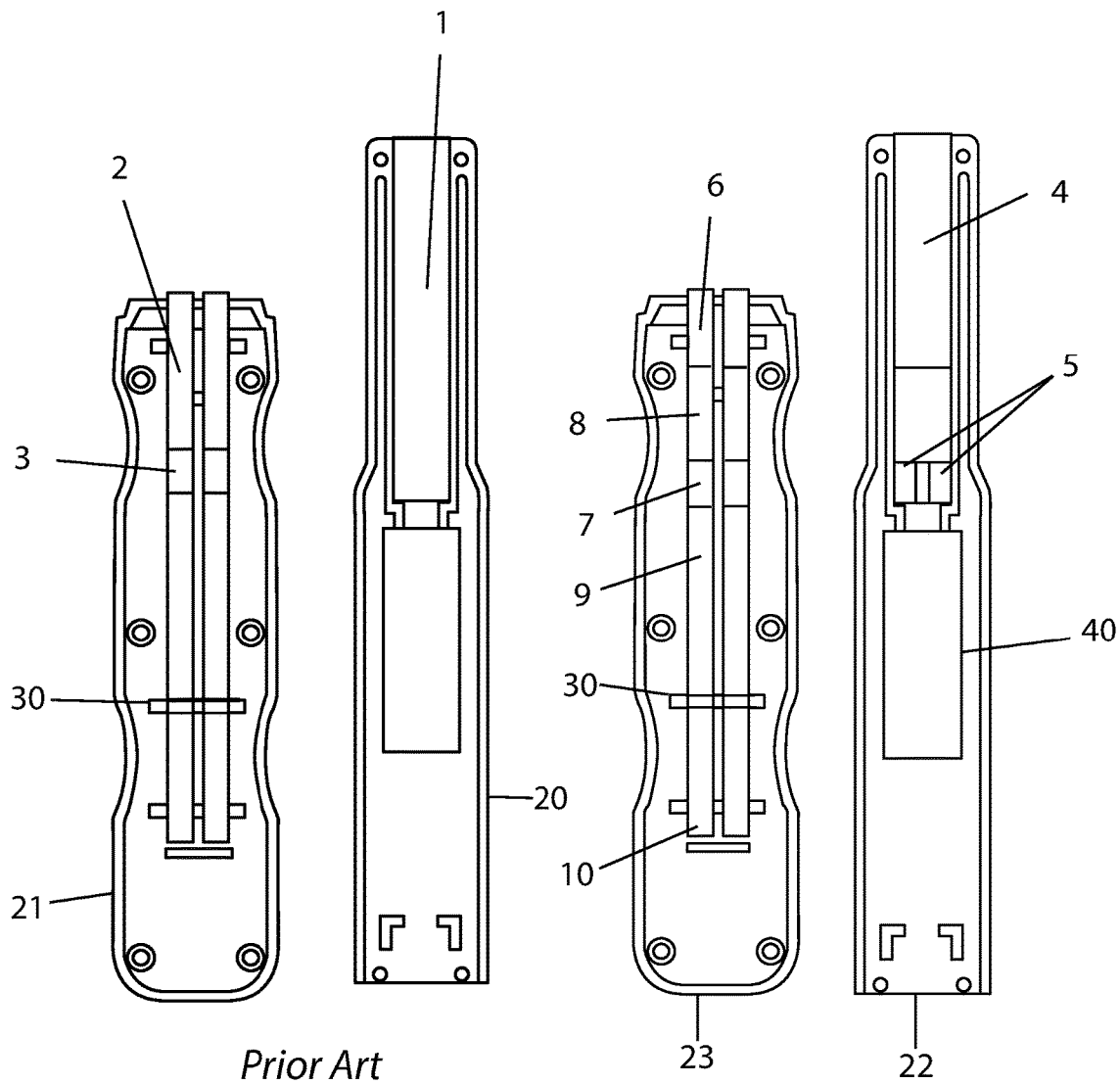

APPARATUS FOR ASSAY STRIP(S) WITH SPECIMEN LOADING TO MULTIPLE ZONES AND RELATED METHODS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF INVENTION

Field of the Invention

The subject matter of this specification is in the field of lateral flow assay strips and related methods.

Background of the Invention

Lateral flow assay tests, also known as a lateral flow immunoassay test or a lateral flow immunochromatography assay test, detect the presence or absence of an analyte in a sample. Lateral flow tests are used for a variety of diagnostic tests, such as a pregnancy test. In general, a lateral flow assay strip contains a collection pad, a sample pad, a conjugate pad, a reaction membrane, and a wick or waste container. The collection pad collects the sample. The sample pad is an absorbent pad that absorbs the test sample. The sample pad is also pre-loaded with chemicals that "pre-condition" the samples so that they are suitable for reaction conditions when they travel downstream. The conjugate pad contains specific antibodies (or antigens) that are conjugated to nanoparticles (tracers), which are commonly conidial gold, and correspond with a specific target analyte in order to ensure a chemical reaction between the target analyte and its antibody. A reaction membrane is where the anti-target analyte antibodies (or protein-conjugated target analytes) are immobilized in a line that crosses the membrane to act as a capture zone or test line. A wick is an absorbent pad that collects the sample that has traveled through the reaction zones.

Once a sample is collected, the lateral flow of the sample is initiated by capillary action so that the sample passes through the conjugate pad and reaction membrane.

Current lateral flow assay strips only have one sample pad, so a specimen will move from the sample pad and enter one side of the conjugate pad before eventually flowing to the reaction membrane. This method is effective, but there are other methods to achieve increased sensitivity. U.S. Pat. No. 6,248,598 by Bogema provides an immunoassay that may collect saliva and test multiple analytes, however, Bogema does not allow for multiple specimen loading points on both sides of a conjugate pad, which results in increased sensitivity of results. Thus, there is a need to increase the sensitivity of the test results for lateral assay strips by increasing the number and locations of sample pads in relation to the conjugate pad.

SUMMARY OF THE INVENTION

In view of the foregoing, it is an object of the present invention to provide a lateral flow assay device with multiple zones for specimen loading.

It is another object of the present invention to provide a lateral flow assay device with sample pads or specimen loading zones located on opposite sides of a conjugate pad.

It is another object of the present invention to provide a lateral flow assay device with increased sensitivity.

BRIEF DESCRIPTION OF THE FIGURES

The manner in which these objectives and other desirable characteristics can be obtained is explained in the following description and attached figures in which:

FIG. 1 is an overhead view of opposing cassettes of a prior art assay strip.

FIG. 2 is an overhead view of one embodiment of opposing cassettes of the lateral flow assay device.

Figure 3:
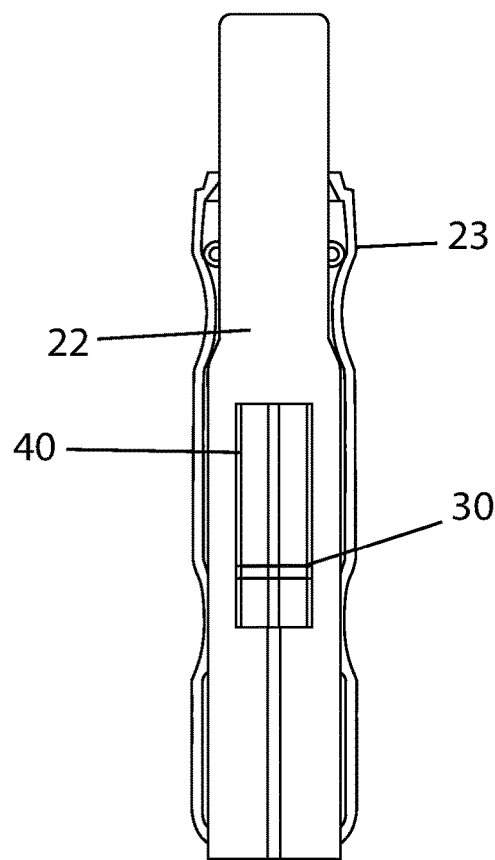
FIG. 3 is a top view of one embodiment of the lateral flow assay device when the opposing cassettes are engaged.

It is to be noted, however, that the appended figures illustrate only typical embodiments of the disclosed assemblies, and therefore, are not to be considered limiting in their scope, for the disclosed assemblies may admit to other equally effective embodiments that will be appreciated by those reasonably skilled in the relevant arts. Also, figures are not necessarily made to scale.

DETAILED DESCRIPTION OF THE INVENTION

Generally, disclosed is a lateral flow assay device with at least one collection pad that may communicate with two sample pads (or one sample pad and one conjugate pad) that are located on opposite sides of a conjugate pad.

FIG. 1 is an overhead view of the inside of opposing cassettes of a lateral flow assay device of prior art. Referring to FIG. 1, prior art lateral flow assay devices have one collection pad 1 on a first cassette 20, which will correspond with the sample pad 2 on a second cassette 21. In use, a user will collect a sample (i.e., saliva or urine) on the collection pad 1, wherein the collection pad 1 corresponds with the sample pad 2. There may be a variable number of test strips within a device to test for multiple analytes, however, in one embodiment, there are two test strips in FIG. 1. Therefore, when a test is conducted on a device of prior art, the sample will be collected at the sample pad 2 on the upstream side of the conjugate pad 3. In a typical competition test for small molecule drugs, the conjugate pad contains antibody-gold conjugates and the membrane is bound with a drug-carrier protein complex. After the sample pad 2 absorbs a drug negative sample that does not contains drug analytes, the sample will flow towards the conjugate pad 3. The sample then flows through to the test line 30, where the bound analyte-carrier protein complexes are immobilized and the antibody-gold conjugates will bind to the analyte-carrier protein complex forming a colored line or lines, which indicate negative results. If the sample pad 2 absorbs a drug positive sample that contains drug analytes, the sample will flow towards the conjugate pad 3, and the analytes will bind the antibodies, which will make the antibodies binding sites not available to bind to the analytes on the membrane downstream. The sample then flows through to the test line 30, where the bound analyte-carrier protein complexes are immobilized and the analyte-bound antibody-gold conjugates will not be able to bind to the analyte-carrier protein complexes. Thus, a colored line will not be formed, indicating positive results. Lateral flow assay devices of prior art may feature a window to view the results of the test on a test line 30.

FIG. 2 is an overhead view of the inside of opposing cassettes of the lateral flow assay device of this disclosure. Referring to FIG. 2, in one embodiment, the device contains two collection pads. The first collection pad 4 and the second collection pad 5 may have an empty space between them. In one embodiment, if there are multiple test strips, as shown in FIG. 2, then collection pad 5 may be split up into two collection pads, so that particles from the conjugate pad 8 of one test strip will not flow across and onto the other test strip. In another embodiment, if there is only one test strip, then collection pad 5 may be comprised of one pad. The first collection pad 4 on the first cassette 22 may be configured to engage with the first sample pad 6 on the second cassette 23 and the second collection pad 5 may be configured to engage with the second sample pad 7. The space between the first collection pad 4 and the second collection pad 5 may correspond with the conjugate pad 8. The sample pads 6,7 are composed of an absorbent material to absorb the specimen from the collection pads 4,5. The conjugate pad 8 will hold the antibodies that bind with a corresponding analyte in the sample. In another embodiment, there may be a window on the top of the first cassette 22 where the collection pads 4,5 (or a collection pad) are located, so that when the cassettes 22,23 are engaged, a sample can be collected through the window to the collection pads 4,5.

Still referring to FIG. 2, the device also features a reaction membrane 9, which contains a matrix to immobilize at least one type of binding particle, which may be the binding antibody or the binding analyte, or both. The lateral flow assay device also contains a wick 10, which is composed of an absorbent material, that absorbs the sample after it has flowed through the test strip. In a preferred embodiment, the first cassette 22 may feature a viewing window 40, that enables a user to see the test line 30 to evaluate whether there is a presence or absence of an analyte in the specimen. In a preferred embodiment, the test strips also feature a control line 50 (See FIG. 4), wherein the line captures a particle that shows the reaction conditions.

FIG. 3 is a top view of the first cassette 22 and the second cassette 23 of FIG. 2 engaged. In one embodiment, when the cassettes are engaged, a user may view the test line 30 and control line 50 through a viewing window 40. The test line 30 may be a colored marker and indicates when a positive detection has occurred by changing or revealing a color.

Figure 4:
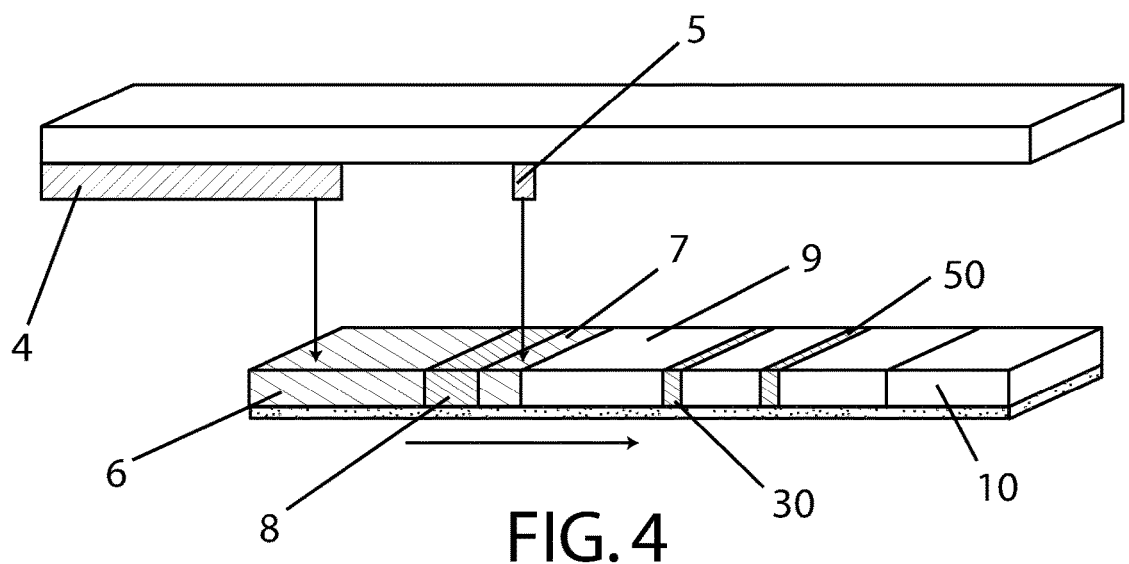
FIG. 4 is an illustrative diagram of how one embodiment of the lateral flow assay device operates.

FIG. 4 is an illustration of how the lateral flow assay device is used. Referring to FIG. 4, there may be two collection pads 4,5 that are separated from each other. After a specimen is collected, a user may engage the collection pads 4,5 (or a single collection pad) to the corresponding sample pads 6,7 by vertically pressing down on the collection pads 4,5 until they engage with the corresponding sample pads 6,7 or by sliding the collection pads 4,5 (or a single collection pad) in place with the sample pads 6,7. After the sample pads 6,7 absorb the sample, the sample will flow downstream (represented by the arrow) via capillary action. The result of the specimen being added from both ends of the conjugate pad 8 is a more sensitive positive result because more of the analytes bind with the antibodies. With the sample pads 6,7 located on both sides of the conjugate pad 8, the specimens located upstream from the conjugate pad 8 will travel towards and through the conjugate pad 8 and the antibodies will bind with the analytes, and as this occurs, the specimen, analyte-bound antibody-gold, and analyte unbound antibody-gold will flow though sample pad 7 towards the reaction membrane 9. The unbound antibody-gold from sample pad 8 will have an opportunity to bind with the analytes of the specimen on the sample pad 7 that is downstream from the conjugate pad 8 and between the conjugate pad 8 and the reaction membrane 9. This becomes an additional location for specimens to be loaded and allows for more analytes to bind because any unbound antibodies will be pushed through the sample pad 7, which may result in a more sensitive positive result.

In use, in a preferred embodiment, when the collection pads 4,5 with the specimen are engaged with the corresponding sample pads 6,7, the specimen is added to and engaged with the sample pad that is between the conjugate pad 8 and the reaction membrane 9, to induce a more sensitive result.

In an alternative embodiment, the lateral flow assay device may feature one collection pad (i.e., the collection pad 1 of prior art) on a first cassette 22, which, when engaged with a second collection pad 7 on a second cassette 23, may contact the two sample pads 6,7 at the same time or at different times by relative sliding between the top collection pad and the bottom test strips so that the sample pads 6,7 absorb the specimen. In one embodiment, the collection pad or pads may slide within the first cassette 22. In another embodiment, the test strip may slide within the second cassette 23.

Figure 5:
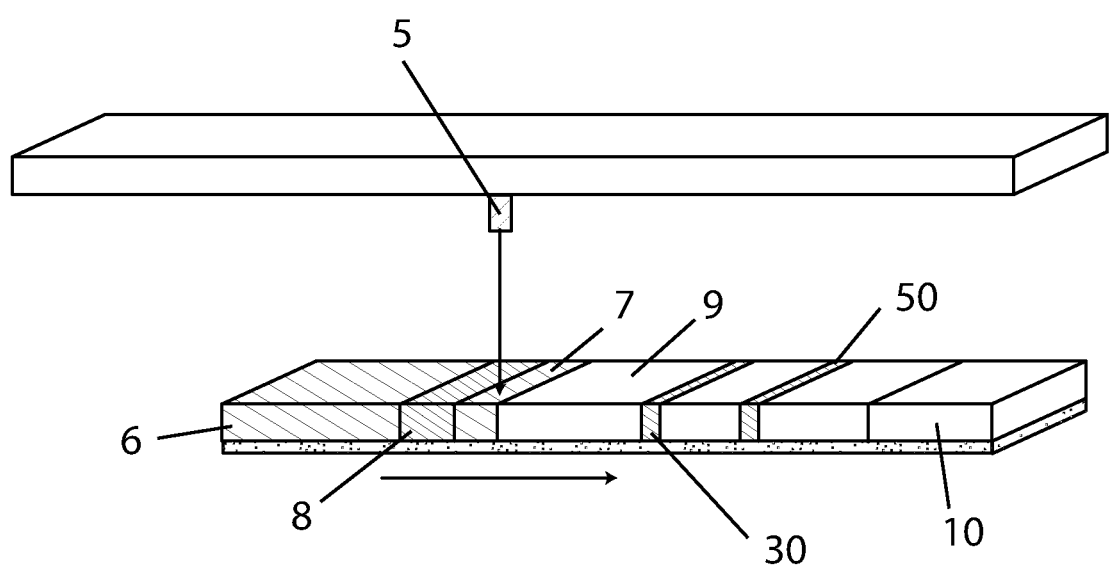
FIG. 5 is an illustrative diagram of how an alternative embodiment of the lateral flow assay device operates.

FIG. 5 is an illustration of another embodiment of the lateral flow assay device. In this embodiment, there may be one collection pad 5 and two sample pads 6,7. A specimen may be added to the collection pad 5 and the collection pad 5 may be engaged with the sample pad 7 that is downstream from the conjugate pad 8 and in between the conjugate pad 8 and reaction membrane 9. When engaged, the analytes from the conjugate pad 8 bind and interact with the antibodies in the specimen absorbed in sample pad 7, and the analytes will also be pulled downstream via capillary action through the test strip.

FIGS. 2 & 3 illustrate a lateral flow assay device with multiple test strips, which are designed for multiple test targets, accordingly, the cassette 22 with the collection pads may feature multiple strips of collection pads to correspond with the multiple test strips. In another embodiment, the lateral flow assay device may feature one test strip on a cassette, and accordingly, the opposing cassette may feature one strip with collection pads.

In use, after collection of a specimen to the collection pads 4,5, there are several methods to engage the collection pads 4,5 with the sample pads 6,7. In one embodiment, a user may align the collection pads 4,5 of a cassette 22 with the sample pads 6,7 of another cassette 23 and vertically press down on the cassette 22 with the collection pads 4,5 so that they engage with the sample pads 6,7.

In an alternative embodiment, a cassette may have one collection pad, so after a user collects a specimen on the collection pad, the user may align the collection pad with the second sample pad between the conjugate pad and the reaction membrane and then press down on the cassette with the collection pad so that the collection pad engages with the second sample pad. Once engaged, the user may then slide the cassette with the collection pad towards the first sample pad, whereby the collection pad contacts and engages with the first sample pad.

In another embodiment, a cassette may have two strips of collection pads corresponding with two test strips. After collection of a specimen, the user may slide the cassette with the collection pads along cassette with the test strips, so that the collection pads contact both the second and the first sample pads of the respective strips.

In an alternative embodiment, there may be one collection pad for each strip on a cassette, so when the specimen is collected, a user may slide along the cassette with the test strips so that the collection pads engage with the second sample pad and then the first sample pad.

In one embodiment, a cassette may have a strip station that holds the test strips. The strip station may slide within the cassette to engage with a corresponding cassette's collection pad. The cassettes may feature a stopper that abuts an edge of a cap containing a reagent, so that when the cassette is inserted into a cap, the cassette may reach the edge of the cap and stop penetration of the cassette, and the strip station may move within the cassette. Accordingly, the collection pads may be engaged with the test strips and slide along the test strips.

The lateral assay device may be used with solid or liquid specimens.

Other features will be understood with reference to the drawings. While various embodiments of the method and apparatus have been described above, it should be understood that they have been presented by way of example only, and not of limitation. Likewise, the various diagrams might depict an example of an architectural or other configuration for the disclosed method and apparatus, which is done to aid in understanding the features and functionality that might be included in the method and apparatus. The disclosed method and apparatus is not restricted to the illustrated example architectures or configurations, but the desired features might be implemented using a variety of alternative architectures and configurations. Indeed, it will be apparent to one of skill in the art how alternative functional, logical or physical partitioning and configurations might be implemented to implement the desired features of the disclosed method and apparatus. Also, a multitude of different constituent module names other than those depicted herein might be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "module" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

The claims filed herewith are incorporated by reference in their entirety into the specification as if fully set forth herein.

I claim:

1. An apparatus for detecting at least one analyte comprising:
    a test strip that is further defined by:
    a conjugate pad;
    a first sample pad and a second sample pad, wherein the conjugate pad is positioned between the first and second sample pads and where the second sample pad is downstream relative to the first sample pad and the conjugate pad;
    a reaction membrane positioned downstream from the conjugate pad;
    at least one test line positioned downstream from the reaction membrane; and,
    at least two collection pads (a) that include a first collection pad that is placed in a first position so that the first collection pad engages the first sample pad so that said at least one analyte is communicated to the first sample pad, (b) that includes a second collection pad that is placed in said first position so that the second collection pad engages said second sample pad so that said at least one analyte is communicated to the second sample pad, (c) that are movable to a second position so that the second collection pad engages the first sample pad while in the second position so that said at least one analyte is communicated to the first sample pad to drive a flow of the analyte downstream.

2. An apparatus of claim 1, wherein the second sample pad is located between the conjugate pad and the reaction membrane, wherein the at least one collection pad also engages the second sample pad so that the analyte is also communicated to the second sample pad.

3. An apparatus of claim 1, wherein there are multiple test strips.

4. An apparatus of claim 1, wherein there are multiple strips with at least one collection pad.

\* \* \* \* \*